United States Patent [19]

Ortega

[11] Patent Number: 4,837,032

[45] Date of Patent: Jun. 6, 1989

[54] THEOPHYLLINE SUSTAINED RELEASE TABLET

[75] Inventor: Aracelis M. Ortega, Caracas, Venezuela

[73] Assignee: Farval AG, Zug, Switzerland

[21] Appl. No.: 825,909

[22] Filed: Feb. 4, 1986

[51] Int. Cl.$^4$ .......................... A61K 9/22; A61K 9/26
[52] U.S. Cl. ..................................... 424/469; 424/470; 424/486; 424/489; 424/494; 424/497; 514/263
[58] Field of Search ............... 424/469, 470, 486, 489, 424/494, 497; 514/263

[56] References Cited

U.S. PATENT DOCUMENTS

| | | | |
|---|---|---|---|
| 2,809,916 | 10/1957 | Hermelin | 167/82 |
| 3,062,720 | 11/1962 | Costello | 167/82 |
| 3,109,775 | 11/1963 | Shepard et al. | 167/82 |
| 3,577,514 | 5/1971 | Robinson | 424/22 |
| 3,909,444 | 9/1975 | Anderson et al. | 252/316 |
| 4,259,314 | 3/1981 | Lowey | 424/469 |
| 4,261,970 | 4/1981 | Ogawa et al. | 424/19 |
| 4,389,393 | 6/1983 | Schor et al. | 424/480 |
| 4,415,547 | 11/1983 | Yu et al. | 424/19 |
| 4,465,660 | 8/1984 | David et al. | 424/15 |
| 4,547,358 | 10/1985 | David et al. | 424/472 |
| 4,587,118 | 5/1986 | Hsiao | 424/462 |
| 4,610,870 | 9/1986 | Jain et al. | 424/468 |
| 4,666,705 | 5/1987 | De Crosta et al. | 424/470 |
| 4,692,337 | 9/1987 | Ukigaya et al. | 424/469 |
| 4,704,284 | 11/1987 | Beatty et al. | 424/469 |
| 4,708,874 | 11/1987 | De Haan et al. | 424/470 |
| 4,710,384 | 12/1987 | Rotman | 424/469 |

*Primary Examiner*—Shep K. Rose

[57] ABSTRACT

Compressed tablets from which theophylline is released at a steady rate with twelve hour dosing intervals are disclosed. The tablets contain 43 to 50 weight percent theophylline; 10 to 20 weight percent water insoluble polymer; 10 to 15 weight percent of a polymer selected from the group consisting of water soluble polymers and hydrophilic gel formers which swell in water; and 5 to 15 weight percent acid insoluble polymer having carboxylic groups. The tablet may additionally contain 5 to 9 weight percent hydrophobic lubricant. A preferred composition contains: 43 to 50 weight percent theophylline; 10 to 20 weight percent polyvinyl acetate; 10 to 15 weight percent polyvinylpyrrolidine; 5 to 15 weight percent cellulose acetate phthalate and optionally contains 5 to 7 weight percent of a lubricant mixture containing stearic acid, magnesium stearate and talc.

13 Claims, 2 Drawing Sheets

THEOPHYLLINE SUSTAINED RELEASE TABLET

FIELD OF THE INVENTION

This invention relates to a sustained release tablet for oral delivery of a pharmaceutical. In particular, the invention provides a polymeric composition for sustained release of theophylline.

STATE OF THE ART

Many systems for controlled or sustained release of pharmaceuticals are taught in the art. Some involve enteric or other coatings which delay release until a given set of conditions exist. Others involve polymeric matrices from which the drug diffuses over a period of time.

Examples of prior art matrices include those disclosed in U.S. Pat. Nos. 2,809,916, 3,062,720, 3,577,514 and 3,909,444. U.S. Pat. No. 2,809,916 describes the manufacture of sustained release tablets formed from granules of medicament end enteric, water-insoluble excipients (including cellulose acetate phthalate) by repeatedly mixing, drying and crushing the medicament and excipient.

U.S. Pat. No. 3,062,720 describes the formation of sustained release tablets from medicament, insoluble solid fatty materials and fillers. Sustained release is accomplished by maintaining a "solubility factor" within a specified range. The solubility factor in turn is dependent on the solubility and weight percent of each of the ingredients.

U.S. Pat. No. 3,577,514 describes a sustained release tablet comprising up to 70% active ingredient, 15 to 50% hydrophobic dissolution retardant, such as natural and synthetic waxes, resins and plastics, 0.1 to 5% acid-insoluble release agent, such as cellulose acetate phthalate, 5 to 15% water soluble binder, such as polyvinyl pyrrolidone and, optionally, lubricants such as talc and magnesium stearate. Theophylline is among the active materials used in the tablet.

U.S. Pat. No. 3,909,444 describes microcapsules which contain a continuous matrix of water soluble polymeric material (such as polyvinyl pyrrolidone) in which finely divided particles of active are dispersed. Some of the active particles are enteric coated (including esters and half esters of cellulose acetate phthalate) and the microcapsules are coated with a water-soluble polymer (such as polyvinyl acetate).

Examples of theophylline release systems, other than those described above are set forth in U.S. Pat. Nos. 3,109,775, 4,261,970, 4,415,547 and 4,465,660. U.S. Pat. No. 3,109,775 describes a tablet for release of theophylline. The tablet may be composed of the theophylline medicament having a retardant coating. The theophylline is coated onto a sugar/starch pellet by means of an adhesive such as cellulose acetate phthalate or polyvinyl pyrrolidone. The pellet may then be coated, for example with cellulose acetate phthalate which will not dissolve in stomach juices.

U.S. Pat. No. 4,261,970 describes a sustained release theophylline granule containing a metal salt of a fatty acid and ehtyl cellulose.

U.S. Pat. No. 4,415,547 describes a sustained release tablet composed of encapsulated pellets and a tableting mixture. The pellets are a sugar-starch bead coated with a first coat of 75 to 90% theophylline and 1 to 35% polyvinyl pyrrolidone and a second coat of from 1 to 10% polyvinyl pyrrolidone, 1 to 60% ethyl cellulose and 30 to 98% dusting powder.

U.S. Pat. No. 4,465,660 describes nondisintegrating theophylline tablets which remain intact during dissolution over an extended period. The tablets are formed of crystalline pulverulent theophylline without tableting aid or other carriers.

The present invention provides compressed tablets from which theophylline, after oral administration, is released at a gradual, constant rate independent of the pH to which it is exposed. The tablets are easily manufactured and permit twelve hour dosing intervals with minimal variability in theophylline blood levels.

SUMMARY OF THE INVENTION

This invention relates to a pharmaceutical tablet containing theophylline. The tablet comprises: 43 to 50 weight percent theophylline; 10 to 20 weight percent water insoluble polymer; 10 to 15 weight percent of a polymer selected from the group consisting of water soluble polymers and hydrophilic gel formers which swell in water; and 5 to 15 weight percent acid insoluble polymer having carboxylic groups. The tablet may additionally contain 5 to 9 weight percent hydrophobic lubricant. A preferred composition contains: 43 to 50 weight percent theophylline; 10 to 20 weight percent polyvinyl acetate; 10 to 15 weight percent polyvinylpyrrolidine; 5 to 15 weight percent cellulose acetate phthalate and optionally contains 5 to 7 weight percent of a lubricant containing stearic acid, magnesium stearate and talc.

The tablets are preferably formulated by (a) wet granulating a mixture of the theophylline and the acid insoluble polymer wiht an alcoholic solution containing part of the hydrophilic gel former or water soluble polymer (b) mixing the remaining hydrophilic gel former or water soluble polymer with the water insoluble polymer (c) mixing the compositions resulting from (a) and (b), and (d) compressing the mixture resulting from (d) into tablets. When orally administered to a patient every twelve hours, relatively uniform blood levels are maintained during prolonged therapy.

DETAILED DESCRIPTION OF THE INVENTION

Figure 1:
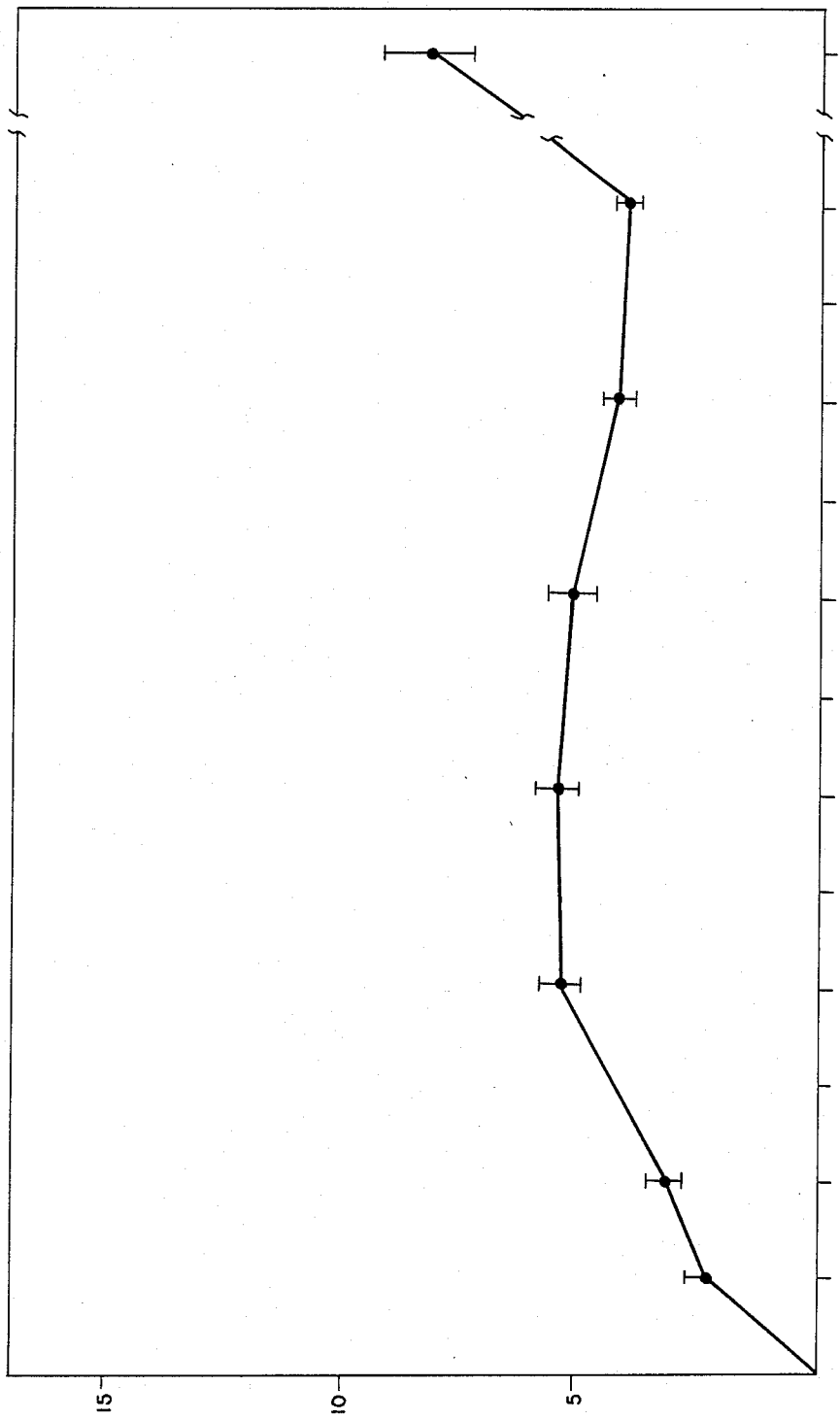
FIGS. 1 and 2 are charts of blood levels of theophylline at various time intervals following administration of the tablets of the invention.

This invention provides sustained release theophylline tablets. The tablets produce relatively uniform blood levels of theophylline over extended periods of therapy with oral administration at intervals of about twelve hours.

The controlled steady release is achieved by means of a polymeric matrix from which the tablet is formed. Because of its composition, the tablet tends to swell and slowly erode rather than disintegrating. Erosion proceeds for an extended period of time with release of theophylline by a diffusion process. The tablet disintegrates into particles only after several hours.

The tablet comprises a combination of materials, specifically a water insoluble polymer, a polymer having carboxylic groups which is acid insoluble but dissolves in neutral or alkaline medium, a water soluble or a swellable hydrophilic gel forming polymer, and optionally a hydrophobic lubricant. The materials are combined with theophylline in the following proportions to achieve the beneficial steady release characteristics of the invention:

(a) 43 to 50 weight percent theophylline;
(b) 10 to 20 weight percent water insoluble polymer;
(c) 10 to 15 weight percent of a polymer selected from the group consisting of water soluble polymers and hydrophilic gel formers which swell in water; and
(d) 5 to 15 weight percent acid insoluble polymer having carboxylic groups.

The water insoluble polymer is believed to serve as a retardant against drug dissolution. The acid insoluble polymer retards drug dissolution in the stomach while allowing dissolution in intestinal fluid. The water soluble polymer swells and dissolves thereby permitting controlled drug dissolution as the gastro-intestinal fluids penetrate and erode the tablet. The hydrophobic lubricant may also retard dissolution by preventing effective wetting of the drug.

In effect, the tablet of the invention does not disintegrate but rather swells and slowly erodes releasing the drug by a diffusion process. Only after several hours does the tablet disintegrate into particles. In in vitro tests using gastro-intestinal fluids the theophylline is characteristically released at a rate of 12±5 percent per hour regardless of pH.

Water insoluble polymers suitable for use in the invention are those which are not digested as they pass through the gastro-intestinal tract. Suitable polymers include polyvinyl acetate, polyvinyl alcohol, vinyl chloride/vinyl acetate copolymers, acrylate polymers and copolymers, methacrylate polymers and copolymers, copolymers of ethyl methacrylate and copolymers of methyl methacrylate. The preferred polymer is polyvinyl acetate, preferably at levels of 10 to 20 weight percent of the tablet, with about 15 weight percent being most preferred.

Acid insoluble polymers for use in the invention include those polymers which have carboxylic groups and which, while acid resistant, dissolve in a neutral or alkaline medium. Examples of such polymers are various esters, including cellulose acetate phthalate, hydroxy propyl methyl celllulose phthalate, esters of acrylic acid copolymers and esters of methacrylic acid copolymers. The preferred material is cellulose acetate phthalate at levels of 5 to 15 weight percent, most preferably at a level of about 15 weight percent.

The water soluble polymer or gel forming polymer which swells in water may be polyvinylpyrrolidone, or cellulose derivatives such as hydroxypropyl methyl cellulose, methyl cellulose or sodium carboxy methyl cellulose. The preferred material is polyvinylpyrrolidone at levels of 10 to 15 weight percent, most preferably about 15 weight percent.

As previously noted, the tablet of the invention may also include a hydrophobic lubricant. Suitable lubricants include talc USP, fatty acids, salts or fatty acids, mineral oil, and hydrogenated vegetable oils. An example of a suitable fatty acid material is stearic acid or its magnesium salt. The most preferred lubricant is a mixture of stearic acid, magnesium stearate and talc USP, optimally in a weight ratio of 3:1:0.5.

The most preferred formulation contains 50 percent anhydrous theophylline, 15 percent cellulose acetate phthalate, 15 percent polyvinylpyrrolidone and 5% of a lubricant mixture containing 3 parts stearic acid, 0.5 parts magnesium stearate and 1.0 part talc USP.

The tablets of the invention may be prepared by comminuting the theophylline with the acid insoluble polymer, preferably to a particle size of less than 30 mesh. The resulting mixture may then be blended and wet granulated with a portion of the film former in a solution such as ethyl alcohol in the case of polyvinylpyrrolidone. The granulate may then be sized through a sieve, optimally 16 mesh, mixed with the remaining film former, the insoluble polymer (also optimally powdered to less than 30 mesh) and the lubricant. The resulting mixture may then be compressed using a standard rotary tablet press. Preferably the tablets are compressed to a hardness of 4 to 10 kg (Erweka Tester).

The tablets of the invention are orally administered in the amounts necessary to achieve a particular blood level. Once the blood level is achieved, it can be maintained by repeated oral administration of the tablet at a dose interval of 12 hours. The optimum dosage size must be determined by observing the therapeutic results achieved and the side effeccts encountered and/or by blood serum analysis. Therapeutically required blood levels are between 5 and 20 mcg/ml.

the following examples are illustrative of the invention and is advantages.

EXAMPLES

Example 1

A mixture of 30 kg of theophylline and 9 kg of cellulose cetate phthalate was granulated with 12 kg of a 25% solution of polyvinyl pyrrolidone in ethanol in a high shear mixer for 10 minutes. The wet mass was dried in a fluid bed dryer at 40°–50° C. for 30 minutes. The dried granulate was sized through a 16 mesh sieve, and then transferred to a V-blender. 9 kg of polyvinyl acetate (particle size less than 30 mesh) was added plus 6 kg of polyvinylpyrrolidone and 3 kg of the lubricant mix (stearic acid: talc: magnesium stearate 3:1:0.5). All the ingredients were mixed for 20 minutes. The granulate so obtained was compressed into tablets using a conventional tablet press to a tablt hardness within the range of 4 to 10 kg (Erweka hardness tester).

The foregoing batch will provide three hundred thousand 100 mg tablets or one hundred fifty thousand 200 mg tablets or seventy-five thousand 300 mg tablets. Tablets can be compressed using standard round flat punches or any other shape; round planar having a bisect score is the preferred configuration for the tablets.

Example II

The rate of drug dissolution was determined using in vitro Dissolution Test Method II USP as described in USP XXI. The method involves placing a tablet in a container in 900 ml fluid at 37° C. and using a paddle type agitator operated at 100 r.p.m. The method involves either one or several pH changes during the run. Aliquots of dissolution medium are removed at intervals, filtered, and analyzed spectrophotometrically for dissolved theophylline using a wave length of 271±1 nm and comparing with a standard reference curve prepared by measurement of the absorption of various solutions of pure theophylline having various concentrations in the same fashion as the test solutions.

Dissolution test involving one pH change

The tablets were contacted with USP artificial gastric fluid (pH 1.2, without enzymes) for two hours, when with USP artificial intestinal fluid (pH 7.5, without enzymes) at 37° C. At the end of each hour's testing an aliquot of the fluid containing the dissolved drug was taken, filtered, and quantitatively assayed by spectrophotometric method at 271±1 nm.

The results, obtained for the release of theophylline are represented in Table I. The figures in parenthesis are the standard deviations.

TABLE I

| Time/hour | pH | Cumulative amount of theophylline released percent | Amount of theophylline dissolved/hour percent |
|---|---|---|---|
| 1 | 1.2 | 17.2 (2.3) | 17.2 |
| 2 | 1.2 | 22.5 (1.4) | 5.3 |
| 3 | 7.5 | 36.7 (4.9) | 14.2 |
| 4 | 7.5 | 48.7 (2.0) | 12.0 |
| 5 | 7.5 | 59.2 (1.4) | 10.5 |
| 6 | 7.5 | 70.9 (1.9) | 11.7 |
| 7 | 7.5 | 81.0 (1.6) | 10.1 |
| 8 | 7.5 | 90.0 (2.2) | 10.0 |

Dissolution test involving several pH changes

The tablets were contacted for one hour with each solution at 37° C. as described before. At the end of each hour the medium was changed for a fresh fluid kept at 37° C. Solutions were artificial gastric fluid (without enzymes), artificial intestinal fluid (without enzymes) and mixtures of both.

The first hour the tablets were contacted with artificial gastric fluid adjusted to pH 1.3. The second hour the fluid was replaced for a mixture of gastric and intestinal fluid (46:54) pH 2.5. The third hour the fluid was replaced for a mixture of gastric and intestinal fluid (20:80) pH 6.8. The fourth hour the medium used was a mixture of gastric and intestinal fluid (6:94) pH 7.25. The fifth hour and thereafter the medium used was artificial intestinal fluid.

The results obtained for release of theophylline are represented in Table II.

TABLE II

| Time/hours | pH | Cumulative amount of theophylline released (%) | Amount of theophylline released/hour percent |
|---|---|---|---|
| 1* | 1.30 | 17 | 17 |
| 2 | 2.50 | 24 | 7 |
| 3 | 6.80 | 36 | 12 |
| 4 | 7.25 | 52 | 16 |
| 5 | 7.50 | 64 | 12 |
| 6 | 7.50 | 76 | 12 |

Example III

Single and multiple dose study I

An open single dose cross-over clinical study employing 12 healthy volunteers was conducted to test "in vivo" performance of the tablets prepared according to the present invention. An immediate release theophylline product served as control.

Twelve young adults aged 19 to 31 years old were selected for the experiment. Each volunteer was evaluated with a physical examination, medical history, hepatic and renal function, complete blood chemistry and cardiovascular examination including E.K.G.

For each subject a cross-over test period with the immediate release theophylline control standard was conducted. Test periods were separated by wash out periods of one week. The individuals received the immediate release product one day and the controlled release product a week later after a wash out period.

Ingestion of medication and xanthine containing food was excluded three days prior to the treatment. Subjects fasted from bedtime the night before until 2 hours after the first blood sample.

A single dose of 7.9±0.07 mg/kg of the test product was administered to each subject with 200 ml of water at 6 a.m. Blood samples of sufficient volume to deliver 5 ml of plasma were drawn immediately prior to drug administration and at 1, 2, 4, 6, 8, 10 and 12 hours after administration.

| Details of Subjects Single and Multiple Dose Study I | | | | |
|---|---|---|---|---|
| Subject | Sex | Age | Weight (kg) | Dose (mg/kg) |
| 1 | F | 19 | 57 | 7.02 |
| 2 | M | 20 | 77 | 7.79 |
| 3 | F | 28 | 49 | 8.16 |
| 4 | F | 23 | 48 | 8.33 |
| 5 | M | 21 | 63 | 6.35 |
| 6 | F | 31 | 53 | 7.55 |
| 7 | F | 28 | 53 | 7.55 |
| 8 | F | 27 | 46 | 8.70 |
| 9 | F | 23 | 48 | 8.33 |
| 10 | F | 27 | 70 | 8.57 |
| 11 | F | 19 | 48 | 8.33 |
| 12 | M | 21 | 72 | 8.33 |

The day of administration of the sustained release tablets, each individual received another identical dose 12 hours after the first dose and then dosing was repeated every 12 hours for 5 days.

Blood samples were taken the third and the fifth day of treatment 6 hours after the morning dose. Plasmas were analyzed for theophylline by a high pressure liquid chromatographic method from Frutkoff et al., Israel J. Med. Sc. 1982, 18: 639-641. The results are set forth in the following table:

| | Average Theophylline concentration in plasma, mcg/ml (± standard error). | |
|---|---|---|
| Time (hours) | Control | Test Tablet |
| 1 | 4.78 (0.96) | 2.37 (0.30) |
| 2 | 7.25 (0.81) | 3.21 (0.27) |
| 4 | 6.82 (0.68) | 5.40 (0.43) |
| 6 | 4.50 (1.08) | 5.52 (0.38) |
| 8 | 3.34 (1.30) | 5.26 (0.46) |
| 10 | 2.72 (1.81) | 4.25 (0.33) |
| 12 | 1.35 (1.52) | 4.04 (0.21) |
| 54 | — | 8.32 (1.00) |
| 102 | — | 8.47 (1.43) |

A graph (FIG. 1) was prepared of plasma theophylline concentration vs time. Areas under the curve from 0 to 12 hours were determined by a standard mathematical method and were used to calculate the relative bioavailability % in 12 hours for the sutained release tablet, assuming 100% for the immediate release:

| | Single Dose Bioavailability | | | |
|---|---|---|---|---|
| Product | Cmax (mcg/ml) | tmax (hours) | AUCo-12 (hrs. mg/L) | Relative Bioavailability (% in 12 hours) |
| Control | 7.25 ±0.81 | 2 | 51.77 ±17.71 | 100 |
| Test Tablet | 5.52 | 6 | 50.82 | 98 |

| Single Dose Bioavailability | | | | |
|---|---|---|---|---|
| Product | Cmax (mcg/ml) | tmax (hours) | AUCo-12 (hrs. mg/L) | Relative Bioavailability (% in 12 hours) |
| | ±0.38 | | ±11.68 | |

Cmax = mean maximal plasma concentration
tmax = mean time to maximal concentration
AUCo-12 = area under the plasma concentration curve from zero to 12 hours The above results show that the tablets prepared according to the present invention performed "in vivo" as a sustained release theophlline medication, reaching blood levels within effective therapeutic range after a chronic treatment at a dosing interval of every 12 hours.

Multiple dose study II

A multiple dose study was conducted employing three asthmatic patients, in order to test steady state plasma concentrations of theophylline and fluctuation % around the mean, achieved with 200 mg tablets prepared according to this invention.

| Details of the Subjects | | | |
|---|---|---|---|
| Subject | Sex | Age (years) | Weight (kg) |
| 1 | M | 24 | 58 |
| 2 | M | 16 | 56 |
| 3 | F | 42 | 61 |

In a preliminary test the subjects received an I.V. bolus infusion in order to determine the clearance rate and the half life of theophylline in plasma:

| Subject | plasma t-½ (hrs) | clearance rate (L/h) |
|---|---|---|
| 1 | 7.29 | 1.65 |
| 2 | 8.92 | 2.23 |
| 3 | 8.58 | 1.13 |

Patients selected for the experiment were non smokers and free of disease other than asthma. Medications of any kind including theophylline were suppressed 7 days prior to the treatment. Xanthine containing food were excluded from their diet three days prior and throughout the experiment.

Each subject received a dose of 400 mg every 12 hours for 5 days. The fifth day a blood sample was taken before the morning dose and then 1, 2, 3, 4, 6, 8, 10 and 12 hours after the dose.

Figure 2:
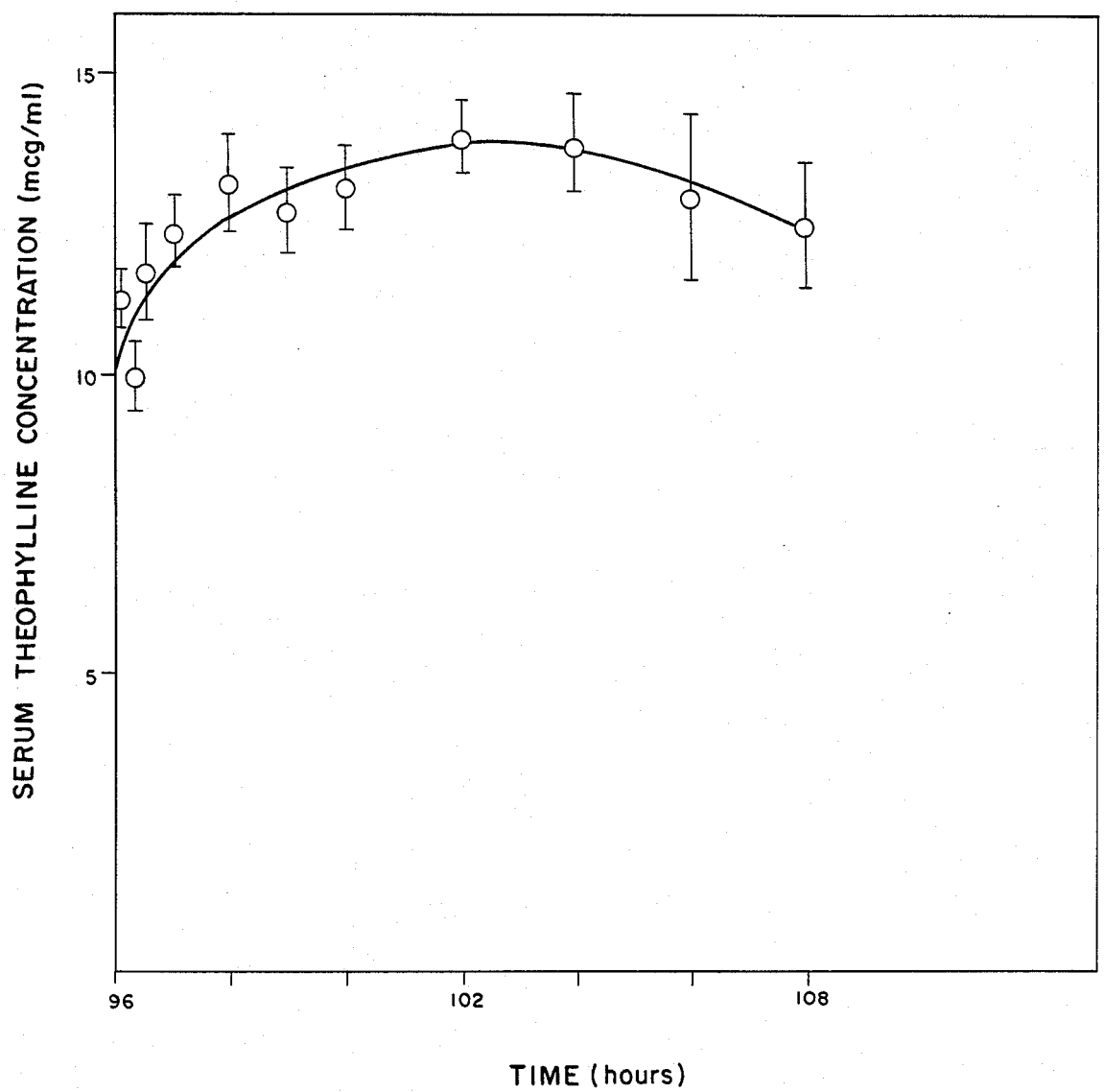

Plasmas were analyzed for theophylline as indicated above. A graph (FIG. 2) prepared with plasma theophylline concentration vs time shows clearly that a steady state plasma concentration within effective therapeutic range was reached.

| Multiple Dose Bioavailability of Theophylline | | | | |
|---|---|---|---|---|
| Subject | Cpss (mcg/ml) | Cmax (mcg/ml) | Cmin (mcg/ml) | Fluctuation %* at steady state | Tmax (hours) |
| 1 | 13.15 ±1.76 | 15.63 | 11.24 | 39.0 | 4 |
| 2 | 13.64 ±1.21 | 15.31 | 12.02 | 27.4 | 6 |
| 3 | 12.20 | 13.36 | 10.53 | 26.8 | 8 |
| | ±1.07 | | | | |

Fluctuation % at s.s. = [(Cmax - Cmin)/ Cmin] × 100
Cmax = maximal plasma concentration
Cmin = minimal plasma concentration
Cpss = mean steady state plasma concentration
Tmax = time of peak plasma concentration The results of this experiment clearly show that the tablets prepared according to this invention when administered on a 12 hours dosage interval, achieves steady state plasma theophylline concentrations within the generally recommended therapeutic range of 10–20 mcg/ml. The mean time of peak plasma concentration (Tmax) at steady state was 6±2 hours.

What is claimed is:

1. A pharmaceutical tablet from which theophylline is released by diffusion in an amount effective for not less than about a twelve hour period from a gel-forming granulate which swells and erodes for an extended period of time, said granulate consisting essentially of:
   (a) 43 to 50 weight percent theophylline;
   (b) 10 to 20 weight percent water insoluble polymer selected from the group consisting of polyvinyl acetate, polyvinyl alcohol, vinyl chloride/vinyl acetate copolymers, acrylate and methacrylate polymers and copolymers, and ethyl and methyl methacrylate copolymers;
   (c) 10 to 15 weight percent of polyvinyl pyrrolidone; and
   (d) 5 to 15 weight percent acid insoluble polymer having carboxylic groups.

2. The pharmaceutical tablet of claim 1 wherein the polymer is polyvinyl acetate.

3. The pharmaceutical tablet of claim 1 wherein the acid insoluble polymer is selected from the group consisting of cellulose acetate phthalate, hydroxypropylmethyl cellulose phthalate and esters of acrylic and methacrylic acid copolymers.

4. The pharmaceutical tablet of claim 1 wherein the acid insoluble polymer is cellulose acetate phthalate.

5. The pharmaceutical tablet of claim 1 further comprising 5 to 9 weight percent hydrophobic lubricant.

6. The pharmaceutical tablet of claim 5 wherein the lubricant is selected from the group consisting of talc, fatty acids, salts of fatty acids, mineral oil and hydrogenated vegetable oils.

7. The pharamceutical tablet of claim 5 wherein the fatty acid is stearic acid.

8. The pharmaceutical tablet of claim 6 wherein the lubricant comprises:
   (a) 3 parts stearic acid;
   (b) 0.5 parts magnesium stearate; and
   (c) 1.0 part talc USP.

9. The pharmaceutical tablet of claim 1 comprising:
   (a) 43 to 50 weight percent theophylline;
   (b) 10 to 20 weight percent polyvinyl acetate;
   (c) 10 to 15 weight percent polyvinylpyrrolidine; and
   (d) 5 to 15 weight percent cellulose acetate phthalate.

10. The pharmaceutical tablet of claim 1 comprising:
   (a) 50 weight percent theophylline;
   (b) 15 weight percent polyvinylacetate;
   (c) 15 weight percent polyvinyl pyrrolidone;
   (d) 15 weight percent cellulose acetate phthalate; and
   (e) 5 weight percent lubricant.

11. A method of maintaining relatively uniform blood levels of theophylline in a host comprising
(a) formulating a theophylline table from which theophylline is released by diffusion in an amount effective for at least about 12 hour periods said tablet being formed from a gel-forming granulate which erodes for an extended period of time, said granulate consisting essentially of:
(i) 43 to 50 weight percent theophylline;
(ii) 10 to 20 weight percent water insoluble polymer selected from the group consisting of polyvinyl acetate, polyvinyl alcohol, vinyl chloride/vinyl acetate copolymers, acrylate and methacrylate polymers and copolymers, and ethyl and methyl methacrylate copolymers;
(iii) 10 to 15 weight percent of polyvinyl pyrrolidone; and
(iv) 5 to 15 weight percent acid insoluble polymer having carboxylic groups.
(b) orally administering one or more of said tablets to a host at twelve hour intervals.

12. The method of claim 11 wherein the tablet is formulated by:
(a) wet granulating a mixture of the theophylline and the acid insoluble polymer with an alcoholic solution containing part of the polyvinyl pyrrolidone;
(b) mixing the remaining polyvinyl pyrrolidone with the water insoluble polymer;
(c) mixing the compositions resulting from (a) and (b) and;
(d) compressing the mixture resulting from (d) into tablets.

13. The method of claim 12 wherein 5 to 9 weight percent hydrophobic lubricant is added to the mixture prior to compression.

* * * * *